(12) United States Patent
Al-Mahmood

(10) Patent No.: US 7,855,184 B2
(45) Date of Patent: *Dec. 21, 2010

(54) ANTISENSE OLIGONUCLEOTIDES CAPABLE OF INHIBITING THE FORMATION OF CAPILLARY TUBES BY ENDOTHELIAL CELLS AND METHODS OF TREATING OPHTHALMIC AND DERMATOLOGICAL DISEASES

(75) Inventor: Salman Al-Mahmood, Paris (FR)

(73) Assignee: Gene Signal International SA, Epalinges (CH)

( * ) Notice: Subject to any disclaimer, the term of this patent is extended or adjusted under 35 U.S.C. 154(b) by 149 days.

This patent is subject to a terminal disclaimer.

(21) Appl. No.: 11/931,844

(22) Filed: Oct. 31, 2007

(65) Prior Publication Data

US 2009/0082292 A1    Mar. 26, 2009

Related U.S. Application Data

(63) Continuation-in-part of application No. 10/735,512, filed on Dec. 12, 2003, now Pat. No. 7,417,033, which is a continuation of application No. PCT/FR02/02067, filed on Jun. 14, 2002.

(30) Foreign Application Priority Data

Jun. 14, 2001   (FR) ................................. 01 07805

(51) Int. Cl.
*C07H 21/02* (2006.01)
*C07H 21/04* (2006.01)
*A61K 31/70* (2006.01)
*C12Q 1/68* (2006.01)
*C12N 5/00* (2006.01)

(52) U.S. Cl. .................. 514/44 A; 435/6; 435/375; 435/377; 536/23.1; 536/24.1; 536/24.5

(58) Field of Classification Search ........................ None
See application file for complete search history.

(56) References Cited

U.S. PATENT DOCUMENTS 5,998,148 A    12/1999   Bennett et al.

FOREIGN PATENT DOCUMENTS

| EP | 1 010 433 A1 | 6/2000 |
| WO | 92/13083 | 8/1992 |
| WO | 96/35791 | 11/1996 |

OTHER PUBLICATIONS

Consuelo D'Ambrosio et al., *Transforming Potential of the Insulin Receptor Substrate $I^1$*, Cell Growth & Differentiation, vol. 6, May 1995, pp. 557-562.

Ewa Surmacz et al., *Overexpression of Insulin Receptor Substrate 1 (IRS-I) in the Human Breast Cancer Cell Line MCF-7 Induces Loss of Estrogen Requirements for Growth and Transformation*, Clinical Cancer Research, vol. 1, Nov. 1995, pp. 1429-1436.

William C. Wallace et al., *Amyloid Precursor Protein Requires the Insulin Signaling Pathway for Neurotrophic Activity*, Molecular Brain Research, 1997, vol. 52, pp. 213-227.

Gert Wolf et al., *PTB Domains of IRS-1 and She Have Distinct but Overlapping Binding Specificities*, The Journal of Biological Chemistry, Nov. 1995, vol. 270(46), pp. 27407-27410.

Mary K. Nolan et al., *Differential Roles of IRS-1 and SHC Signaling Pathways in Breast Cancer Cells*, Int. J. Cancer, 1997, vol. 72, pp. 828-834.

*Primary Examiner*—Sean R McGarry
(74) *Attorney, Agent, or Firm*—Young & Thompson

(57) ABSTRACT

A pharmaceutical composition blocks angiogenesis and contains as an active agent at least one nucleotide sequence from nucleic acid molecule SEQ ID NO. 3, fragments thereof containing at least twelve contiguous nucleotides and derivatives thereof; and nucleic acid sequences containing at least twelve contiguous nucleotides of the nucleic acid molecule SEQ ID NO 30 and derivatives thereof.

24 Claims, 5 Drawing Sheets

Subconjunctival injections
of antisense oligonucleotides
(60 μM)

Subconjunctival injections
of sense oligonucleotides
(60 μM)

Topical applications of
antisense oligonucleotide
(200 μM)

Topical applications of
sense oligonucleotide
(200 μM)

No treatment

Subconjunctival injections
of PBS

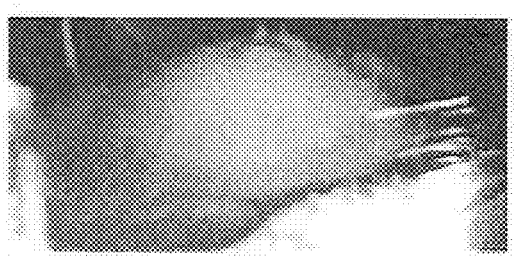
Day 4 AS [antisense] 60    FIG.5A
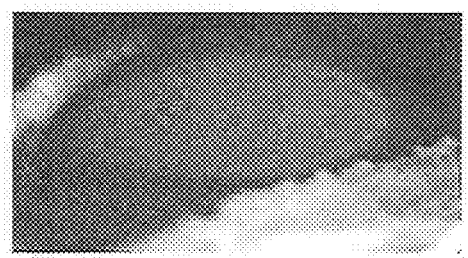
Day 9 AS [antisense] 60    FIG.5F
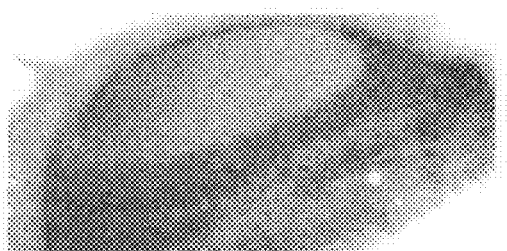
Day 4 AS [antisense] 200    FIG.5B
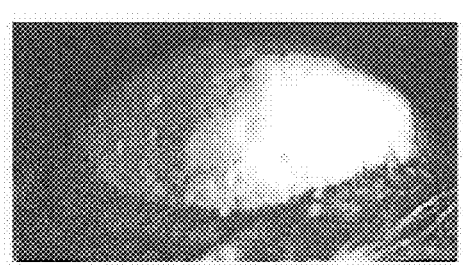
Day 9 AS [antisense] 200    FIG.5G
Day 4 S [sense] 200    FIG.5C
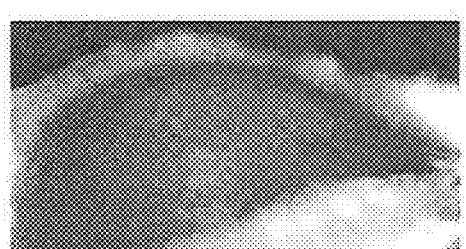
Day 9 S [sense] 200    FIG.5H
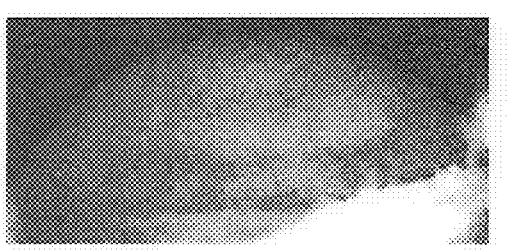
Day 4 PBS    FIG.5D
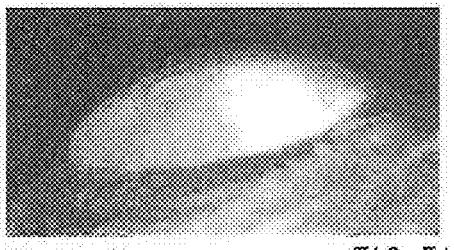
Day 9 PBS    FIG.5I
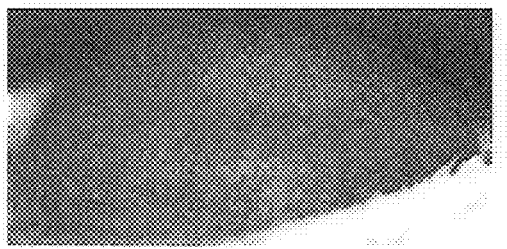
Day 4 No treatment    FIG.5E
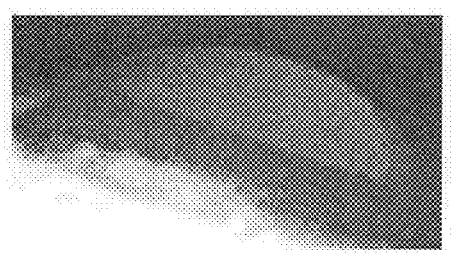
Day 9 No treatment    FIG.5J

ANTISENSE OLIGONUCLEOTIDES CAPABLE OF INHIBITING THE FORMATION OF CAPILLARY TUBES BY ENDOTHELIAL CELLS AND METHODS OF TREATING OPHTHALMIC AND DERMATOLOGICAL DISEASES

RELATED APPLICATION

This is continuation-in-part of U.S. patent application Ser. No. 10/735,512 filed Dec. 12, 2003, which is a continuation of International Application No. PCT/FR02/02067, with an international filing date of Jun. 14, 2002, which is based on French Patent Application No. 01/07805, filed Jun. 14, 2001.

TECHNICAL FIELD

This disclosure relates to antisense oligonucleotides capable of inhibiting the expression of the protein IRS-1 and inhibiting the formation of capillary tubes by endothelial cells. Thus, the disclosure relates to antiangiogenic agents and anti-cell-multiplication agents, particularly, antitumor agents. The disclosure also pertains to pharmaceutical compositions containing the oligonucleotides, methods of treating diseases such as ophthalmic and skin diseases and the use of the oligonucleotides as analysis reagents.

BACKGROUND

Angiogenesis is a fundamental process by means of which new blood vessels are formed. This process is essential in multiple normal physiological phenomena such as reproduction, development and even cicatrization. In these normal biological phenomena, angiogenesis is under strict control, i.e., it is triggered during a short period (several days) and then completely inhibited. However, many pathologies are linked to uncontrolled, invasive angiogenesis: arthritis, a pathology due to the damaging of cartilage by invasive neovessels; diabetic retinopathy or the invasion of the retina by neovessels leading to blindness of patients; neovascularization of the ocular apparatus which is a major cause of blindness. This neovascularization is involved in about twenty different eye diseases. Moreover, the growth and metastasis of tumors which are linked directly to neovascularization are dependent on angiogenesis. The tumor stimulates the growth of neovessels by its own growth. Moreover, these neovessels are escape routes for tumors which thereby join up with the blood circulation and induce metastases in sites remote from the initial tumor focus, such as the liver, lungs or bones.

Angiogenesis, the formation of neovessels by endothelial cells, involves the migration, growth and differentiation of endothelial cells. Regulation of these biological phenomena is directly linked to genetic expression.

SUMMARY

We provide pharmaceutical compositions comprising as an active agent at least one nucleotide sequence selected from the group consisting of nucleic acid molecule SEQ ID NO. 3, fragments thereof comprising at least twelve contiguous nucleotides and derivatives thereof; and nucleic acid sequences comprising at least twelve contiguous nucleotides of the nucleic acid molecule SEQ ID NO 30 and derivatives thereof.

In a preferred aspect, the nucleic acid sequences comprises at least twelve contiguous nucleotides of the nucleic acid molecule SEQ ID NO 30 are selected from the group consisting of SEQ ID NO 31 to SEQ ID NO 44 and fragments thereof comprising at least twelve contiguous nucleotides.

We also provide methods of inhibiting angiogenesis including administering a pharmaceutically effective amount of the pharmaceutical composition to a mammal.

We further provide methods of treating ophthalmic disease including administering a pharmaceutically effective amount of the pharmaceutical composition to a mammal.

We still further provide methods of treating corneal graft rejection, neovascular glaucoma or retinopathy of prematurity comprising administering a pharmaceutically effective amount of the pharmaceutical composition to a mammal.

We yet further provide methods of treating age related macular degeneration or diabetic retinopathy comprising administering a pharmaceutically effective amount of the pharmaceutical composition to a mammal.

We also provide methods of treating dermatological diseases including administering a pharmaceutically effective amount of the pharmaceutical composition to a mammal.

We further provide methods of treating psoriasis or rosacea, comprising administering a pharmaceutically effective amount of the pharmaceutical composition to a mammal.

BRIEF DESCRIPTION OF THE DRAWINGS

Other advantages and characteristics will become clear from the representative examples below in which the term "oligonucleotide" is used to designate the oligonucleotide of SEQ ID NO. 3 and which refer to the attached figures in which:

FIG. 3A shows the culture of untreated endothelial cells,

FIG. 3B shows the culture of endothelial cells stimulated with 3 ng/ml of bFGF,

FIG. 3C shows the culture of endothelial cells incubated with 100 μg/ml of oligonucleotide of SEQ ID NO. 3 for 4 hours and then stimulated with 3 ng/ml of bFGF, FIG. 3D shows the culture of endothelial cells incubated with 100 μg/ml of oligonucleotide of SEQ ID NO. 3 for 4 hours.

FIG. 4A shows the results obtained by subconjunctival injection of an antisense oligonucleotide at a concentration of 60 μm, FIG. 4B shows the results obtained after subconjunctival injection of a sense oligonucleotide at a concentration of 60 μm, FIG. 4C shows the results obtained after topical application of an antisense oligonucleotide at a concentration of 200 μm, FIG. 4D shows the results obtained after topical application of a sense oligonucleotide at a concentration of 200 μm, FIG. 4E illustrates the state of the cornea in the absence of any treatment, FIG. 4F illustrates the state of the cornea when treated with subconjunctival injections of PBS, FIGS. 5A to 5J illustrate the results of the inhibition of corneal neovascularization obtained in different groups of rats after de-epithelialization and limbic resection of the corneas of the rats on day 4 (FIGS. 5A to 5E) and on day 9 (FIGS. 5F to 5J). These are slit lamp photographs showing the comparison of the growth of the vessels in the various groups of rats. Enlargement ×10.

DETAILED DESCRIPTION

Figure 1:
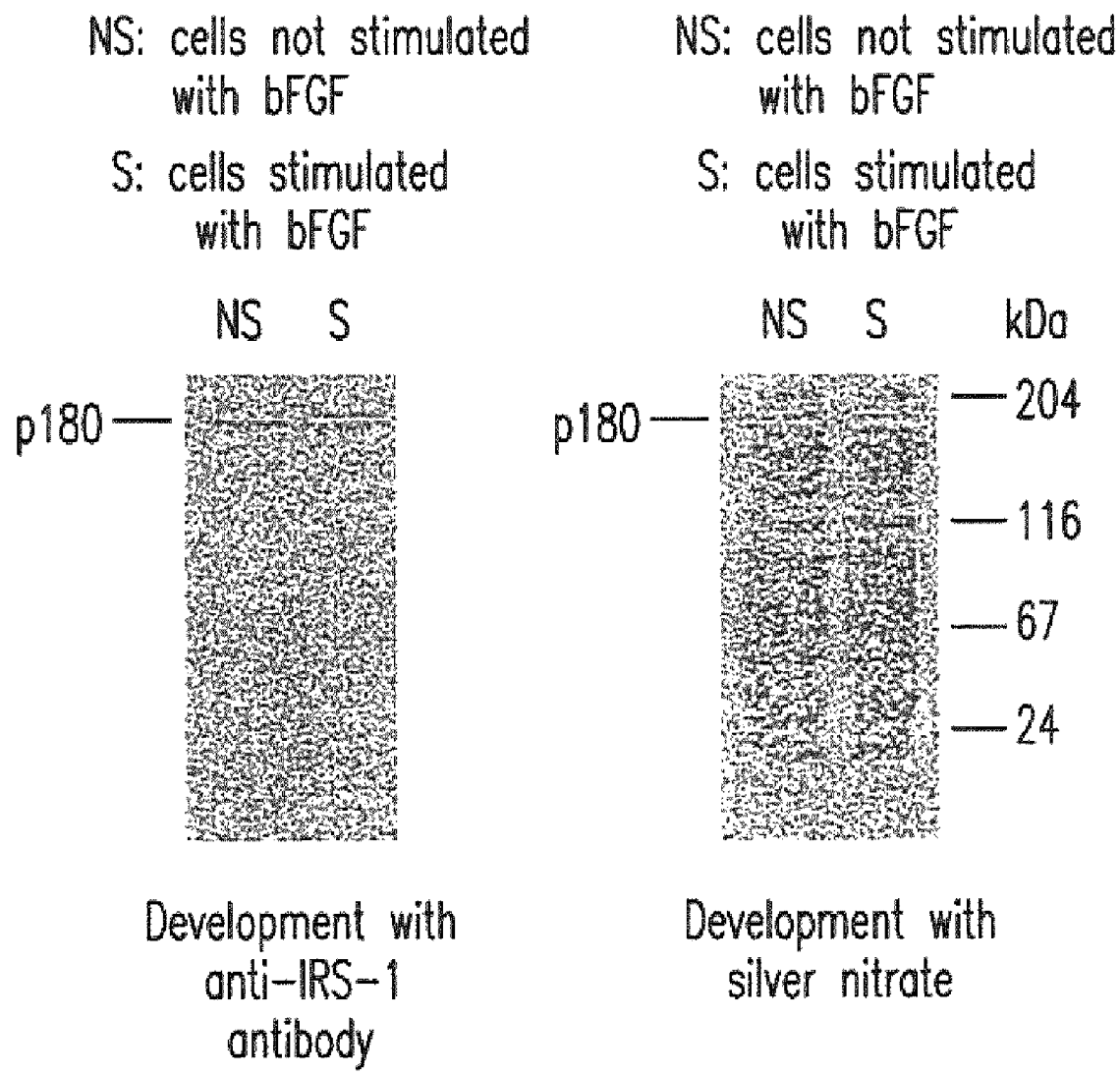
FIG. 1A is a Western Blot of images obtained from supernatant samples stemming from unstimulated cells (track NS) and cells stimulated with bFGF (track S) developed with an anti-IRS-1 antibody.
FIG. 1B is a Western Blot of images obtained after staining with silver nitrate obtained from the same supernatant samples stemming from unstimulated cells (track NS) and cells stimulated with bFGF (track S)

Our work performed made it possible to identify and prepare nucleic acid sequences involved in the regulation of angiogenesis.

Other studies pertaining to angiogenesis have shown a noteworthy expression and phosphorylation at the level of a tyrosine residue of an intracellular 180-kDa protein by endothelial cells cultured on a surface of type I collagen and stimulated by an angiogenic factor such as bFGF. The noteworthy expression and phosphorylation at the level of the tyrosine residue of the intracellular 180-kDa protein accompanies the formation of capillary tubes by the endothelial cells.

That protein is already known as a substrate of the insulin receptor (called IRS-1). It has been partially identified and investigated by certain diabetes researchers (Quon et al., J. Biol. Chem. (1994), 269 (45), 27920-27924). Those authors studied the role of IRS-1 in (i) the translocation of GLUT 4 stimulated by insulin and (ii) the transport of glucose in rat adipose cells. They constructed a plasmid containing:

a double chain oligonucleotide obtained from the sense oligonucleotide of the following sequence SEQ ID NO. ID No. 1: 5'-TCGATGTGAC GCTACTGATG AGTC-CGTGAG GACGAAACTC TGGCCTAG-3' and cDNA coding for human IRS-1, and transfected rat adipose cells with said plasmid to do this.

Our work revealed that the expression of the protein IRS-1 is also induced in endothelial cells when those cells are stimulated by the angiogenic factor bFGF.

We thus provide pharmaceutical compositions active on angiogenesis phenomena comprising as an active agent at least one nucleotide sequence selected from the group consisting of nucleic acid molecule SEQ ID NO.3, fragments thereof comprising at least twelve contiguous nucleotides and derivatives thereof; and nucleic acid sequences comprising at least twelve contiguous nucleotides of the nucleic acid molecule SEQ ID NO 30 and derivatives thereof.

In a preferred aspect, the nucleic acid sequences comprising at least twelve contiguous nucleotides of the nucleic acid molecule SEQ ID NO 30 are selected from the group consisting of SEQ ID NO 31 to SEQ ID NO 44 and fragments thereof comprising at least twelve contiguous nucleotides.

These oligonucleotides have remarkable antiangiogenic and antitumor activities. They are therefore particularly useful in the treatment of diseases linked to invasive angiogenesis not controlled by gene therapy methods including administering to an individual a composition containing at least one of these oligonucleotides.

The disclosure pertains most particularly to the oligonucleotide of formula SEQ ID NO. 3

5'-TATCCGGAGGGCTCGCCATGCTGCT-3', a fragment of this sequence comprising at least 12 contiguous nucleotides or derivatives of this sequence.

The term "derivative" is understood to mean a sequence capable of hybridizing under stringent conditions with one of the above mentioned sequences or with a fragment of these of at least 12 contiguous nucleotides. Derivatives may be derived from insertion, deletion or substitution of nucleic acids. Stringent conditions may be selected, as appropriate, by a person skilled in the art. A low stringent condition is, for example, 42° C., 2*SSC, and 0.1% SDS, and preferably 50° C., 2*SSC, and 0.1% SDS. A high stringent condition is for example 65° C., 2*SSC, and 0.1% SDS.

The disclosure pertains also most particularly to nucleic acid sequences of at least twelve contiguous nucleotides of SEQ ID NO 30 and derivatives thereof, SEQ ID NO 30 having the following formula:

5'-
TAGTACTCGAGGCGCGCCGGGCCCCCAGCCTCGCTGGCCGCGCGCAGTAC

GAAGAAGCGTTTGTGCATGCTCTTGGGTTTGCGCAGGTAGCCCACCTTGC

GCACGTCCGAGAAGCCATCGCTCTCCGGAGGGCTCGCCATGCTGCCACC

G -3'.

The disclosure pertains also most particularly to the oligonucleotide of formula SEQ ID NO. 31

5'- TCTCCGGAGGGCTCGCCATGCTGC -3', a fragment of this sequence comprising at least 12 contiguous nucleotides or derivatives of this sequence.

The disclosure also pertains to the oligonucleotide of formula SEQ ID NO 32

5'- CGGAGGGCTCGCCATGCTGCCACCG -3', a fragment of this sequence comprising at least 12 contiguous nucleotides or derivatives of this sequence.

The disclosure also pertains to the oligonucleotide of formula SEQ ID NO 33

5'- CGGAGGGCTCGCCATGCTGCCACC -3', a fragment of this sequence comprising at least 12 contiguous nucleotides or derivatives of this sequence.

The disclosure also pertains to the oligonucleotide of formula SEQ ID NO 34

5'- CGGAGGGCTCGCCATGCTGCCAC -3', a fragment of this sequence comprising at least 12 contiguous nucleotides or derivatives of this sequence.

The disclosure also pertains to the oligonucleotide of formula SEQ ID NO 35

5'- CGGAGGGCTCGCCATGCTGCCA -3', a fragment of this sequence comprising at least 12 contiguous nucleotides or derivatives of this sequence.

The disclosure also pertains to the oligonucleotide of formula SEQ ID NO 36

5'- CGGAGGGCTCGCCATGCTGCC -3', a fragment of this sequence comprising at least 12 contiguous nucleotides or derivatives of this sequence.

The disclosure also pertains to the oligonucleotide of formula SEQ ID NO 37

5'- CGGAGGGCTCGCCATGCTGC -3', a fragment of this sequence comprising at least 12 contiguous nucleotides or derivatives of this sequence.

The disclosure also pertains to the oligonucleotide of formula SEQ ID NO 38

5'- CGTCCGAGAAGCCATCGCTCTCCGGAG -3', a fragment of this sequence comprising at least 12 contiguous nucleotides or derivatives of this sequence.

The disclosure also pertains to the oligonucleotide of formula SEQ ID NO 39

5'- GCGCAGGTAGCCCACCTTGCGCACGTC -3', a fragment of this sequence comprising at least 12 contiguous nucleotides or derivatives of this sequence.

The disclosure also pertains to the oligonucleotide of formula SEQ ID NO 40

5'- CCCACCTTGCGCACGT -3', a fragment of this sequence comprising at least 12 Contiguous nucleotides or derivatives of this sequence.

The disclosure also pertains to the oligonucleotide of formula SEQ ID NO 41

5'- GAAGAAGCGTTTGTGCATGCTCTTGGGTTT -3', a fragment of this sequence comprising at least 12 Contiguous nucleotides or derivatives of this sequence.

The disclosure also pertains to the oligonucleotide of formula SEQ ID NO 42

5'- GCCCCCAGCCTCGCTGGCCGCGCGCAGTACGAA -3', a fragment of this sequence comprising at least 12 contiguous nucleotides or derivatives of this sequence.

The disclosure also pertains to the oligonucleotide of formula SEQ ID NO 43

5'- TAGTACTCGAGGCGCGCCGGGCCCCC -3', a fragment of this sequence comprising at least 12 contiguous nucleotides or derivatives of this sequence.

The disclosure also pertains to the oligonucleotide of formula SEQ ID NO 44

5'- AGGCGCGCCGGGCCCCC -3', a fragment of this sequence comprising at least 12 contiguous nucleotides or derivatives of this sequence.

All or part of the phosphodiester bonds are advantageously protected. This protection is generally implemented via the chemical route using methods that are known by art. The phosphodiester bonds can be protected, for example, by a thiol or amine functional group or by a phenyl group.

The 5'- and/or 3'-ends of the oligonucleotides are also advantageously protected, for example, using the technique described above for protecting the phosphodiester bonds.

The oligonucleotides can be synthesized using conventional techniques that are known art, for example, using one of the DNA synthesizers marketed by various companies.

Although their mechanism of action has not been entirely elucidated, the oligonucleotides inhibit the expression of the protein IRS-1 within endothelial cells. These oligonucleotides block the formation of neovessels by endothelial cells (i.e., they inhibit angiogenesis) and thus they inhibit the multiplication of tumor cells in mice.

The composition of the invention advantageously comprises as an active agent at least one oligonucleotide as defined above advantageously combined in the composition with an acceptable vehicle.

It was found that the protein IRS-1 represents a cellular constituent which is essential in the angiogenesis process. In fact, inhibition of the expression of the protein IRS-1 by the antisense oligonucleotides leads to the inhibition of the formation of capillary tubes by endothelial cells.

The oligonucleotides and the compositions containing them are thus antiangiogenic agents. They are also anti-cell-multiplication agents, particularly as antitumor agents, and consequently are particularly useful for the treatment of tumors. Thus, the invention includes the use of the oligonucleotides for the preparation of a composition intended for the treatment or prevention of pathologies linked to invasive, uncontrolled angiogenesis such as, as a nonlimitative example: the treatment of tumor vascularization, eye diseases such as those linked to the neovascularization of the ocular apparatus such as retinopathies such as retinopathy of prematurities and diabetic retinopathy, corneal graft rejection, neovascular glaucoma, AMD (age-related macular disease), rheumatoid arthritis, Crohn's disease, atherosclerosis, hyperstimulation of the ovary, skin disease such as rosacea and psoriasis, endometritis associated with neovascularization, restenosis due to balloon angioplasty, tissue superproduction due to cicatrization, peripheral vascular disease, hypertension, vascular inflammation, Raynaud's disease and Raynaud's phenomena, aneurysm, arterial restenosis, thrombophlebitis, lymphangitis, lymphedema, tissue cicatrization and repair, ischemia, angina, myocardial infarction, chronic heart disease, cardiac insufficiencies such as congestive heart failure, age-related macular degeneration and osteoporosis.

The pharmaceutical composition is in a form capable of subcutaneous, intramuscular, intravenous, transdermal or topical administration.

Preferably, the pharmaceutical composition is in a form capable of topical administration.

More preferably, the pharmaceutical composition is in the form of eye drops.

According to one aspect, the pharmaceutical composition of the invention is in the form of a hydrogel. In one embodiment, said hygrogel comprises the active agent, a water-soluble polymer such as carboxymethylcellulose, and water. Preferably, the amount of water-soluble polymer is about 0.001 to about 5 g per 100 g and the amount of water is about 95 to about 99.9 g per 100 g. In another aspect, the hydrogel comprises the active agent, paraffine and vaseline. Preferably, the amount of paraffine is about 40 to about 85 g per 100 g and the amount of vaseline is about 15 g to about 60 g per 100 g.

According to one aspect, the pharmaceutical composition is supplied in bi-compartmental vials, one compartment comprising dry powder of the pharmaceutical composition and the other compartment comprising a solvent such as NaCl, 0.9% solution.

The above pharmaceutical compositions are more particularly implemented in a manner such that they can be administered via the subcutaneous, intramuscular, intravenous, transdermal or topical route, for example. For such administration, use is made of aqueous suspensions, isotonic saline solutions or sterile, injectable solutions containing pharmacologically compatible dispersion agents and/or wetting agents such as, for example, propylene glycol or butylene glycol.

The usual unit dose to be administered contains from about 0.001 mg to about 50 mg of active principle.

According to another aspect, the pharmaceutical composition contains about 0.001 mg/ml to about 10 mg/ml of the active agent, preferably about 0.1 mg/ml to about 5 mg/ml, more preferably about 0.2 to about 4 mg/ml and most preferably about 0.4 mg/ml to 2 mg/ml.

According to another aspect, the total dose per day per eye of the active principle is comprised from about 1 μg to about 500 μg, preferably from about 10 μg to about 250 μg and more preferably from about 40 μg to about 200 μg.

The oligonucleotides are also useful as research reagents, notably for the in vitro study of signalization routes involving the 180-kDa protein, for example, on tumor cells or non-tumor cells transfected by the oligonucleotides. They are also useful for the in vivo study of signalization routes involving the 180-kDa protein in a large number of physiological and pathological phenomena such as angiogenesis or carcinogenesis essentially from the kinase/phosphatase ratio.

The disclosure also relates to methods for inhibiting angiogenesis, comprising administering a pharmaceutically effective amount of the pharmaceutical composition of the invention to a mammal.

The disclosure also relates to methods for treating ophthalmic disease in a subject in need thereof, comprising administering a pharmaceutically effective amount of the pharmaceutical composition to the subject.

According to an aspect, the methods comprise administering at least one drop, preferably two drops per day and per affected eye of a pharmaceutically effective amount of the pharmaceutical composition to the subject.

According to one aspect, the duration of the administration is at least three months, preferably six months.

The disclosure also relates to methods for restoring visual acuity and/or corneal sensitivity in a subject in need thereof, comprising administering a pharmaceutically effective amount of the pharmaceutical composition to the subject.

The disclosure also relates to methods for treating corneal graft rejection in a subject in need thereof, comprising administering a pharmaceutically effective amount of the pharmaceutical composition to the subject.

The disclosure also relates to methods for treating corneal graft rejection in a subject having experienced corneal lesions leading to neovascularization, comprising administering a pharmaceutically effective amount of the pharmaceutical composition to the subject.

According to one aspect, we provide methods for treating corneal graft rejection in a subject suffering from keratitis or keratouveitis, comprising administering a pharmaceutically effective amount of the pharmaceutical composition to the subject, wherein the keratitis or keratouveitis is due to contact lens, bacteria, microorganisms such as Chlamydia, Staphylococcus, Streptococcus, Pseudomonas; viruses, such as herpes simples, herpes zoster; protozoa, such as Onchocerca volvulus, Leishmaniabrasiliensis, Acanthamoeba keratitis; immunologic diseases, such as Stevens-Johnson syndrome, rosacea keratitis; or keratitis or keratouveitis due to trauma and prior surgery, alkali burns, graft rejection and degenerative disorders.

According to an aspect, the method for treating corneal graft rejection comprises the administration of one to two drops per day and per affected eye of the pharmaceutical composition, the composition comprising about 0.1 mg/ml to about 5 mg/ml of the active agent, preferably about 0.2 to about 4 mg/ml and most preferably about 0.4 mg/ml to 2 mg/ml of the active agent.

In a preferred aspect, the pharmaceutical composition comprises about 0.8 mg/ml to about 1 mg/ml of the active agent. In this embodiment, each drop contains about 40 μg to about 50 μg of the active agent. Administration of two drops per day corresponds thus to the administration of about 80 μg to about 100 μg of the active agent per day.

The disclosure also relates to methods for treating neovascular glaucoma or retinopathy of prematurity in a subject in need thereof, comprising administering a pharmaceutically effective amount of the pharmaceutical composition to the subject.

According to an aspect, the methods comprise administration of one to two drops per day and per affected eye of the pharmaceutical composition the composition comprising about 0.1 mg/ml to about 5 mg/ml of the active agent, preferably about 0.2 to about 4 mg/ml and most preferably about 0.4 mg/ml to 2 mg/ml of the active agent.

The disclosure also relates to methods for treating age related macular degeneration in a subject in need thereof, comprising administering a pharmaceutically effective amount of the pharmaceutical composition to the subject.

The disclosure also relates to methods for treating diabetic retinopathy in a subject in need thereof, comprising administering a pharmaceutically effective amount of the pharmaceutical composition to the subject.

The disclosure also relates to methods for treating dermatological diseases in a subject in need thereof, comprising administering a pharmaceutically effective amount of the pharmaceutical composition to the subject.

The disclosure also relates to methods for treating psoriasis in a subject in need thereof, comprising administering a pharmaceutically effective amount of the pharmaceutical composition to the subject.

The disclosure also relates to methods for treating rosacea in a subject in need thereof comprising administering a pharmaceutically effective amount of the pharmaceutical composition to the subject.

In a preferred aspect, the pharmaceutical composition is in the form capable of transdermal or topical administration.

According to one aspect, the pharmaceutical composition comprises about 0.1 mg/ml to about 5 mg/ml of the active agent, preferably about 0.2 to about 4 mg/ml and most preferably about 0.4 mg/ml to 2 mg/ml of the active agent.

EXAMPLE 1

Demonstration of the Induction of the Expression of IRS-1 (the 180-kDa Protein) in Endothelial Cells Resulting from the Stimulation of these Cells with bFGF.

The 180-kDa protein was demonstrated in the following manner:

The endothelial cells were cultured in a 6-well microtitration plate previously covered with type I collagen as described in (Montesano et al., J. Cell. Biol., 1983, 83, 1648-1652). The culture medium was DMEM (Sigma) enriched with 10% of fetal calf serum, 4 mM glutamine, 500 U/ml penicillin and 100 µg/ml streptomycin. After 3 to 4 days of culture, there resulted a semi-confluent layer of endothelial cells. The culture medium of six wells was aspirated and replaced by fresh culture medium. Three wells were enriched with 3 ng/ml of bFGF. After incubation for 48 hours, the wells were washed three times with a phosphate buffer and the cells were used to extract the messenger RNA (mRNA) according to protocols known in the art. The mRNAs were reverse transcribed by a polymerization chain reaction (PCR) using each of four degenerated groups of oligo (dT) (T12MN) (SEQ ID NO: 45) primers, M can be G, A or C; and N is G, A, T and C. Each group of primers is imposed by the base in position 3'(N) with a degeneration in the (M) position. Example: the set of primers in which N=G is constituted by:

```
SEQ ID NO. 24:      5'-TTTTTTTTTTTTGG-3'
SEQ ID NO. 25:      5'-TTTTTTTTTTTTAG-3'
SEQ ID NO. 26:      5'-TTTTTTTTTTTTCG-3'.
```

The cDNAs obtained in this manner were amplified and tagged by means of an arbitrary decamer in the presence of isotopically tagged ATP. The electrophoresis analysis of the cDNAs revealed the presence of an amplified 326-bp cDNA fragment in the sample stemming from the endothelial cells stimulated with bFGF, identified in the attached sequence listing as number SEQ ID NO. 27. However, this same fragment is weakly present or present in the trace state in the sample stemming from the endothelial cells that were not stimulated with bFGF. The sequencing of this fragment and the subsequent interrogation of the databases revealed that this fragment corresponds to a part of an already known gene, coding for the substrate of the insulin receptor (an intracellular 180-kDa protein).

EXAMPLE 2

Demonstration of the Induction of the Expression of IRS-1 (the 180-kDa Protein)

Endothelial cells cultured on a layer of type I collagen stimulated or not stimulated with bFGF (cf. example 1) were lysed in a cellular lyse buffer containing sodium orthovanadate. These solutions were then clarified by centrifugation at 14,000 g for 15 minutes. Supernatant samples stemming from unstimulated cells and cells stimulated with bFGF containing equivalent amounts of proteins were then taken up with an electrophoresis solution containing 2% SDS and 15 mM of dithiothreitol, heated at 100° C. for 5 minutes then deposited on polyacrylamide gel (gradient from 4 to 15% of acrylamide) under denatured conditions (in the presence of 2% SDS). After migration, the proteins were transferred onto a nitrocellulose membrane. The membrane was blocked by incubation at ambient temperature in a 5% milk solution in a PBS buffer. The membrane was then washed three times with a PBS buffer, incubated in a PBS buffer containing 1 µg/ml of anti-IRS-1 monoclonal antibody for 2 hours at ambient temperature and washed three times with a PBS buffer. The proteins were then developed with a secondary anti-isotope antibody coupled to peroxidase. The presence was noted of a protein of molecular weight 180 kDa recognized by the monoclonal anti-IRS-1 antibody in the preparations stemming from the endothelial cells stimulated with bFGF; this protein was weakly present in the preparation stemming from the endothelial cells not simulated with bFGF (FIG. 1).

EXAMPLE 3

Demonstration of the Induction of Phosphorylation at the Level of IRS-1 Tyrosine (the 180-kDa Protein)

Figure 2:
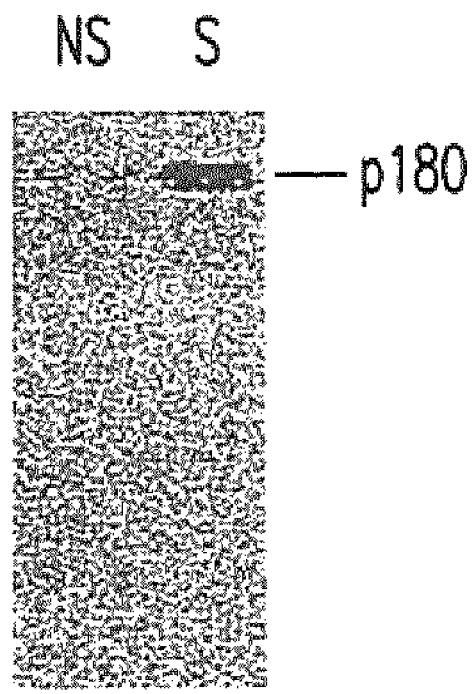
FIG. 2 is a Western Blot of images obtained from supernatant cells stemming from unstimulated cells (track NS) and cells stimulated with bFGF (track B) when the membrane is incubated with an anti-phosphotyrosine monoclonal antibody and developed with an anti-isotype antibody tagged at the peroxidase as indicated in Example 3.

Human endothelial cells cultured on a layer of type I collagen stimulated or not stimulated with bFGF were lysed in a cellular lyse buffer containing sodium orthovanadate. These solutions were then clarified by centrifugation at 14,000 g for 15 minutes (cf example 2). The IRS-1 protein was extracted by means of an anti-IRS-1 monoclonal antibody. This extraction was performed after immunoprecipitation by means of an anti-IRS-1 monoclonal antibody (Sigma). After addition of the anti-IRS-1 antibody coupled to agarose, the suspension was incubated for 2 hours at ambient temperature then centrifuged at 4000 g for 15 minutes. The resultant precipitate was taken up with an electrophoresis solution containing 2% SDS and 15 mM of dithiothreitol, heated at 100° C. for 5 minutes, then deposited on polyacrylamide gel (acrylamide gradient of 4 to 15%) under denaturing conditions (in the presence of 2% SDS). After migration, the proteins were transferred onto a nitrocellulose membrane. The membrane was blocked by incubation at ambient temperature in a 5% milk solution in a PBS buffer. The membrane was then washed three times with a PBS buffer, incubated in a PBS buffer containing 1 µg/1 ml of anti-phosphotyrosine monoclonal antibody for 2 hours at ambient temperature, and then washed three times with a PBS buffer. The proteins were then developed by means of a secondary anti-isotope antibody coupled to peroxidase. It was found that the IRS-1 protein of molecular weight 180 kDa was phosphorylated at the level of the tyrosine residue in the preparations stemming from the endothelial cells stimulated with bFGF; this protein was very weakly phosphorylated at the level of the tyrosine residue in the preparation stemming from the endothelial cells not stimulated with bFGF (FIG. 2).

EXAMPLE 4

Evaluation of the In Vitro Antiangiogenic Activity of the Oligonucleotide

Figure 3A:
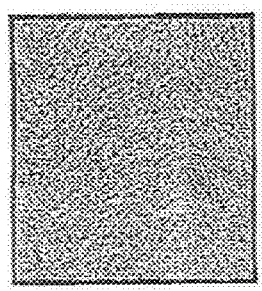
FIGS. 3A to 3D show the images of the cultures on a type I collagen surface of the different lots of endothelial cells.
Figure 3B:
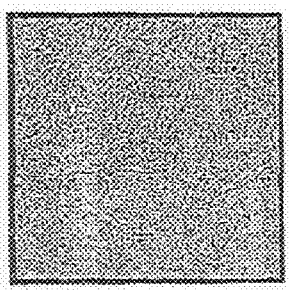
Figure 3C:
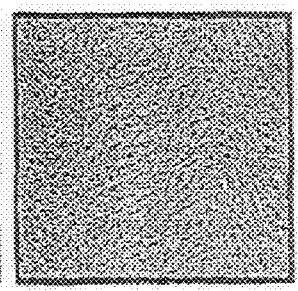
Figure 3D:
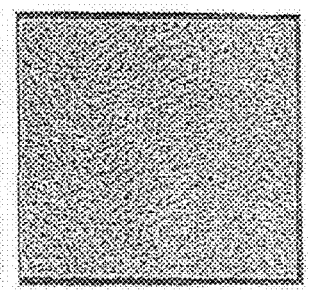
Figure 4A:
FIGS. 4A to 4F illustrate the results of tests of the inhibition of corneal neovascularization in rats.
Figure 4B:
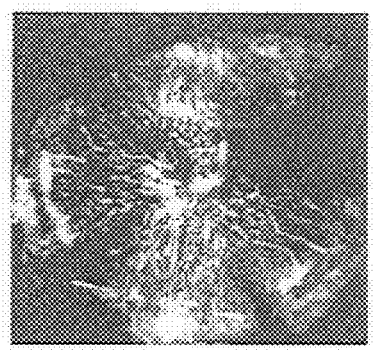
Figure 4C:
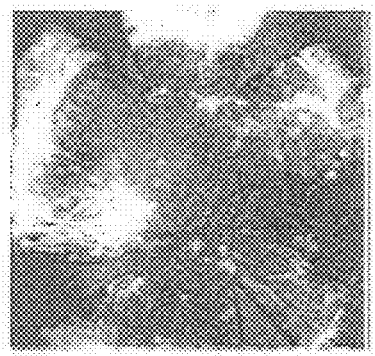
Figure 4D:
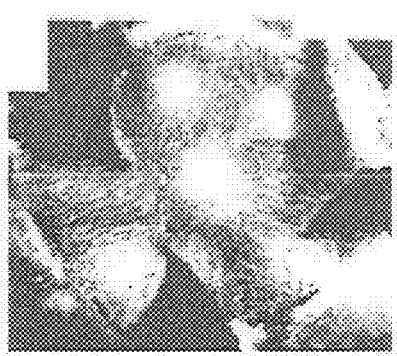
Figure 4E:
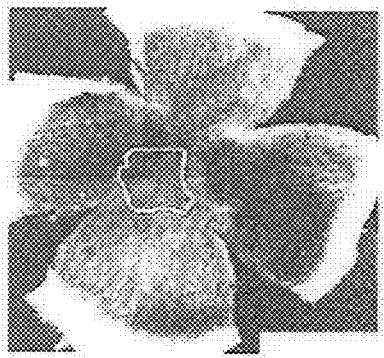
Figure 4F:
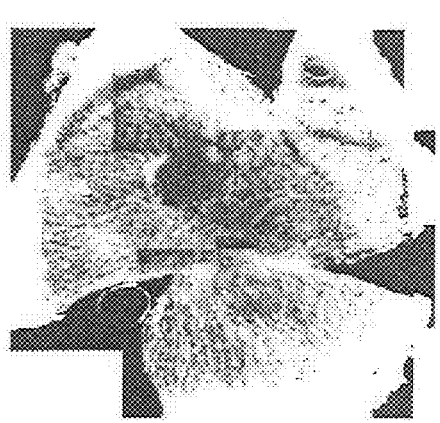

Human endothelial cells were cultured on a layer of type I collagen. The culture wells were divided into four lots on the seventh day of culture:
 Lot 1: Wells corresponding to the culture of untreated endothelial cells (FIG. 3A).
 Lot 2: Wells corresponding to the culture of endothelial cells stimulated with 3 ng/ml of bFGF (FIG. 3B).
 Lot 3: Wells corresponding to the culture of endothelial cells incubated with 100 µg/ml of oligonucleotide of SEQ ID NO. 3 for 4 hours then stimulated with 3 ng/ml of bFGF (FIG. 3C).
 Lot 4: Wells corresponding to the culture of endothelial cells incubated with 100 µg/ml of oligonucleotide of sequence SEQ ID NO. 3 for 4 hours (FIG. 3D).

The various wells were examined by means of an inverted phase optical microscope after 3 to 4 days of culture. Upon reading the results, it was found that the human endothelial cells in lot 2 formed capillary tubes following stimulation with bFGF. It was also found that the oligonucleotide inhibits the formation of neovessels by these same cells stimulated with bFGF in lot 3. Finally, it was found that that the oligonucleotide does not modify in a pronounced manner the growth of the endothelial cells. In fact, the numbers of endothelial cells in the lot 1 wells and in the lot 4 wells were comparable.

EXAMPLE 5

Evaluation of the In vivo Activity of the Oligonucleotide

Three lots of naked mice were used. Each lot was constituted by 5 mice.

Lot no. 1: This lot was used as control. Each mouse was inoculated on day 0 with 200 µl of a suspension of B16 melanoma cells (provided by Institut Gustave Roussy, Villejuif) dispersed in PBS at the level of $10^6$ cells/ml. These mice did not receive subsequent treatment.

Lot no. 2: Each mouse was inoculated subcutaneously on day 0 with 200 µl of a suspension of B16 melanoma cells dispersed in PBS at the level of $10^6$ cells/ml. On day 1, day 2, day 3, day 4, day 5, day 6, day 7, day 8, day 9 and day 10 each mouse received a subcutaneous injection of 200 µl of an oligonucleotide solution diluted in PBS at a concentration of 500 µg/ml. The oligonucleotide injection was performed close to the cell injection site.

Lot no. 3: The mice of this lot were not inoculated with the B16 melanoma cells. However, each of the mice received an injection of 200 µl of an oligonucleotide solution in PBS at a concentration of 500 µg/ml; the injections were performed on day 1, day 2, day 3, day 4, day 5, day 6, day 7, day 8, day 9 and day 10.

The following results were obtained:

In the mice of lot no. 1, the tumor mass developed very rapidly after inoculation. In fact, the tumor mass reached a size of 1.6 to 2.5 cm in diameter after ten days in the mice of said lot no. 1 (untreated mice). The evolution of the tumor mass in the mice of lot no. 2 (mice treated after inoculation by injection of oligonucleotide on day 1, day 2 and day 3), exhibited a clearly lower increase in the volume of the tumor mass. The tumor mass in the mice of lot 2 did not exceed 0.8 cm in diameter on the tenth day. On the fourteenth day, the difference between the tumor mass of the mice of lot no. 2 and those of lot no. 1 was remarkable.

In the mice of lot no. 3 (mice not having received B16 melanoma cells but treated by injection of oligonucleotide for three days), an unexpected general effect was observed on the skin. It was identical to that observed on all of the mice treated with the oligonucleotide (lot 2). The skin had an aged, crumpled appearance. The emergence of hairs was also observed on all of the treated mice. There was a parallelism during the evolution between the regression of the cutaneous signs and the resumption of tumor growth.

Thus, it was found that the oligonucleotide inhibits the development and formation of neovessels by endothelial cells in vitro. The oligonucleotide also has a remarkable in vivo antitumor activity in the naked mouse.

EXAMPLE 6

Evaluation of the Antiangiogenic Oligonucleotide on a Corneal Neovascularization Model in the Rat I employed, modified and analyzed a model of the formation of corneal neovessels in the rat after de-epithelialization and limbectomy (FIGS. 5A to 5J). It is reproducible, allows direct slit-lamp examination and quantification of the neovessels. The details are described below. The model was then used for testing the efficacy of the antiangiogenic agents of the invention. Animals and corneal neovascularization model Male Wister rats (*Rattus norvegicus*), aged five weeks (Charles River France, St-Aubin les Elbeufs, France), free of specific pathogens, were fed and allowed to drink water freely, and maintained in the laboratory animal facility under fixed temperature and humidity conditions, with cycles of 12 hours of light/12 hours of darkness.

The rats were anesthetized with a mixture of ketamine (Kétamine 1000, UVA, Ivry-sur-Seine, France; 128 mg/kg) and chlorpromazine (Largactil 25 mg/ml; Specia Rhône Poulenc, Paris, France; 5 mg/kg), injected via the intramuscular route. A drop of oxybuprocaine (Novésine, Chibret, Clermont-Ferrand, France) was instilled in the right eye. Using an enlargement system (macroscope Wild MPS 51 S, LEICA, Heerbrugg, Switzerland), the corneal epithelium was removed by a microsponge impregnated with 70% ethanol. A 1.5-mm band of conjunctiva, at the limbus, was excised with microsurgical scissors, and the eyelids were closed by a temporary blepharorraphy with a Vicryl 5.0 thread (Dacron, Alcon, Rueil-Malmaison, France). The eye was then rinsed abundantly with 1×PBS, an oxytetracycline cream was applied (Posicycline, Alcon, France) and the blepharorraphy was opened on the fourth day [8, 9].

Treatment by Subconjunctival Injections and Topical Applications of Antiangiogenic Oligonucleotide The rats were divided into 6 groups:

Group A: model+subconjunctival injection of a 60-µM antisense oligonucleotide solution in 1×PBS, Group B: model+topical application of a 200-µM antisense oligonucleotide solution in 1×PBS, Group C: model+subconjunctival injection of a 60-µM sense oligonucleotide solution in 1×PBS, Group D: model+topical application of a 200-µM sense oligonucleotide solution in 1×PBS, Group E: model+subcutaneous injection of 1×PBS, Group F: model without treatment.

All of the rats were subjected to de-epithelialization as described above; the treatment was performed every 24 hours starting on the fourth day and continuing until the ninth day. Neovascularization was examined at the beginning, in the middle and at the end of the protocol by slit-lamp examination; photographs were taken on day 0 and day 9.

Visualization and Quantification of the Neovascularization

The animals were euthanized 10 days after the de-epithelialization by lethal injection of pentobarbital (intraperitoneal injection). In order to fill the microvessels and quantify the corneal neovascularization, the upper part of the animals' bodies were perfused with fluorescein-dextran 2×1,000,000. The eyes were enucleated and immersed in paraformaldehyde/1×PBS 4% for 3 hours, then overnight in 1×PBS. The cornea was then isolated with 1 mm of limbus under surgical microscope and inserted in the flat state between plate and cover by means of 3 to 5 radial incisions. The flat corneas were then examined and photographed using fluorescence microscopy. After the whole corneas were reconstituted, they were scanned and the surfaces were measured by image analysis; a software program (NIH image) was used for the quantification of the neovascularization. For each photo, the total corneal surface was measured three times as was the neovascularized surface; the ratio of the means—neovascularized surface/total corneal surface—was used to obtain the percentage of neovascularization and to measure the inhibition obtained.

Statistical Analysis

The results were expressed as means±SD. The percentages of neovascularized surface/total surface were compared with the nonparametric test of Mann-Whitney. Values of P<0.05 were considered to be significant.

Dilution of the Oligonucleotide

The oligonucleotide was diluted in 1×PBS at pH 7.2. Based on the data in the literature and the experiments performed with other oligonucleotides, it was decided to use a concentration of 60 µM for the subconjunctival injections and a concentration of 200 µM for the topical applications.

Results

Using the model of corneal neovessels, treatment was performed with the 5'-TATCCGGAGGGCTCGCCATGCT-GCT-3' oligonucleotides identified under SEQ ID NO. 3 in the attached sequence listing modified in phosphorothioate form, daily, from day 4 to day 9, according to the following protocol:

Group A: subconjunctival injection of the antisense oligonucleotide at 60 µM (AS 60),
Group B: topical application of the antisense oligonucleotide at 200 µM (AS 200),
Group C: subconjunctival injection of the sense oligonucleotide at 60 µM (S 60),
Group D: topical application of the sense oligonucleotide at 200 µM (S 200),
Group E: subconjunctival injection of 1×PBS (PBS),
Group F: no treatment (0 Tt).

On the tenth day of the protocol, the rats were perfused with a solution of FITC/dextran and then euthanized. The corneas were collected and fixed in a 4% PAF solution. The corneas were then inserted in the flat state between plate and cover in a glycerol solution. The fluorescent neovessels were observed and photographed using the fluorescence microscope. The photographs were scanned and the neovascularization percentages were measured for each animal.

The results observed are presented in Table 1 below:

TABLE 1

|  | Group A AS 60 | Group B AS 200 | Group C S 60 | Group D S 200 | Group E PBS | Group F 0 Tt |
|---|---|---|---|---|---|---|
| Mean | 0.6157 | 0.5058 | 0.9431 | 0.9392 | 0.9552 | 9.9170 |
| SD | 0.2194 | 0.1172 | 0.0964 | 0.0308 | 0.0481 | 0.0751 |
| Number of measurements | 15 | 15 | 15 | 12 | 9 | 9 |
| SEM | 0.0566 | 0.0303 | 0.0249 | 0.0089 | 0.0160 | 0.0250 |

The statistical analysis of the results using a nonparametric Mann-Whitney test yielded the following results:

The subconjunctival injections of 60-µM of the antisense oligonucleotide (A) reduced neovascularization in relation to the control groups E and F (very significant results, P<0.0001 and P=0.0011); topical application of the antisense oligonucleotide at a concentration of 200 µM (B) reduced neovascularization in relation to the control groups E and F (extremely significant results, P<0.0001).

Compared to the subconjunctival administration of the sense oligonucleotide at 60 µM (C) or the topical application of the sense oligonucleotide at 200 µM (D), injection of the antisense oligonucleotide at 60 µM (A) and topical application of the antisense oligonucleotide at 200 µM (B) reduced neovascularization. These results were extremely significant (P<0.0001) (FIGS. 4A to 4F).

The inhibition of neovascularization was not significantly different depending on whether the antisense oligonucleotide was administered via the subconjunctival route (60 µM) or applied topically (200 µM). It was approximately 35% in relation to the controls (E and F).

The subconjunctival injection of the sense oligonucleotide at 60 µM (C) and the topical application of the sense oligonucleotide at a concentration of 200 µM (D) did not modify the neovascularization in relation to the control groups (E and F). In contrast, there was a small effect of the sense oligonucleotide in topical application (D) compared to the sense oligonucleotide in subconjunctival injections (C) (P=0.0117).

Moreover, there was seen in the groups treated with the antisense oligonucleotide (A and B), a smaller diameter and density of the neovessels. Their distribution did not differ in relation to the control groups nor was any difference observed in relation to the level of inflammation (FIG. 4).

Secondary Effects

No noteworthy secondary effects were seen in any of the groups during the two experimental series: after 6 days of treatment at the doses specified above, the skin of the rats was not crumpled, the fur was unchanged and the general condition of the animals was good; they fed normally until the last day and no suspicious mortality was observed. Although neither autopsies nor blood tests were performed, the general status of the animals at the end of the experiments did not suggest hepatic disorders. The only symptom observed was a transitory whitish deposit at the site of the conjunctival injections in 60% of the rats of group A, 60% of the rats of group C and 10% of the rats of group E. This deposit had been resorbed by the end of the experiments in all cases.

This example shows that—contrary to expectations—the subcutaneous injections of antisense oligonucleotide at a concentration of 60 µM did not inhibit neovascularization to a greater extent than the topical application of the antisense oligonucleotide at a concentration of 200 µM.

This can perhaps be explained by the difference in the concentrations employed; but this results suggests also a penetration of the oligonucleotide via the topical route rather than via the limbus. It also suggests the absence of prolonged release of the product from the injection site.

CONCLUSION

The application of the antisense oligonucleotide via the topical route or in subconjunctival injections reduces neovascularization in our model of corneal neovessels in the rat.

The purpose of this study was to test the efficacy of the antisense oligonucleotides stemming from the sequence of the gene IRS-1 on a previously developed model of corneal neovascularization in the rat.

The subject matter of the publications below is incorporated by reference:

1. Aiello L P. Keeping in touch with angiogenesis. *Nat Med* 2000; 6: 379-381.
2. D'Amore P A. Mechanisms of Retinal and Choroidal Neovascularization. *Invest Ophthalmol Vis Sci* 1994; 35(12): 3974-3979.
3. Hélène C. Rational design of sequence-specific oncogene inhibitors based on antisense and antigens oligonucleotides. *Eur. J Cancer* 1991; 27: 1466-1471.
4. Agrawal S, Bunnel B A, Crooke S T, Davidkova G, Gyurko R, Iyer K et al. Antisense oligonucleotides and antisense RNA. Benjamin Weiss edition (Philadelphia, USA) 1997; 1-11, 19-40.
5. Pierga J Y, Cammilleri S, Benyahia B, Magdelénat H. Applications of antisense oligonucleotides in cancer research. *Bull Cancer* 1994; 81: 1023-1042.
6. Robinson G S, Pierce E A, Rook S L, Foley E, Webb R, Smith L E H. Oligodeoxynucleotides inhibit retinal neovascularization in a murine model of proliferative retinopathy. *Proc Natl Acad Sci USA* 1996; 93: 4851-4856.
7. Aiello L P. Vascular endothelial growth factor. *Invest Ophthalmol Vis Sci* 1997; 38: 1647-1652.
8. Amano S, Rohan R, Kuroki M, Tolentino M, Adamis A P. Requirement for vascular endothelial growth factor in wound and inflammation-related corneal neovascularization. *Invest Opthalmol Vis Sci* 1998; 39: 18-22.
9. Hoang-Xuan T, Prisant O. Restoration of corneal epithelium from limbic stem cells. *Med Sci* 1998; 14: 1375-1377.
10. Parry T J, Cushman C, Gallegos A M, Agrawal A B, Richardson M, Andres L E et al. Bioactivity of antiangiogenic ribozymes targeting Flt-1 and KDR in RNA. *Nucleic Acids Research* 1999; 27: 2569-2577.
11. Ozaki H, Seo M S, Ozaki K, Yamada H, Yamada E, Okamoto N et al. Blockade of vascular endothelial cell growth factor receptor signaling is sufficient to completely prevent retinal neovascularization. *Am J Pathol* 2000; 156: 697-707.
12. Berdugo Polak M. Iontophoresis administration of antisense oligonucleotides in the anterior segment of the eye: application to a corneal neovascularization model in the rat. DEA "Biology and Pathology of the Epithelia"; University of Paris VII, Feldmann G; Inserm U450, Director Courtois Y, under the direction of Bellar Cohen F. 2000.

The invention claimed is:

1. A pharmaceutical composition comprising as an active agent at least one nucleotide sequence selected from the group consisting of a nucleic acid sequence comprising at least twelve contiguous nucleotides of the nucleic acid molecule SEQ ID NO 30 and a derivative of said nucleic acid sequence capable of hybridizing with IRS-1 sequence at a temperature from 42° C. to 65° C., 2× SSC and 0. 1% SDS.

2. The pharmaceutical composition according to claim 1, wherein said nucleic acid sequence comprising at least twelve contiguous nucleotides of the nucleic acid molecule SEQ ID NO 30 is selected from the group consisting of SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44 and fragments thereof comprising at least twelve contiguous nucleotides.

3. The pharmaceutical composition according to claim 1, which contains about 0.001 mg to about 50 mg of the active agent and is in a form capable of subcutaneous, intramuscular, intravenous, transdermal or topical administration.

4. The pharmaceutical composition according to claim 1, which is in the form of eye drops.

5. The pharmaceutical composition according to claim 1, which is supplied in bi-compartmental vials, one compartment comprising dry powder of the pharmaceutical composition and the other one comprising solvent.

6. The pharmaceutical composition according to claim 1, which contains about 0.001 mg/ml to 10 mg/ml of the active agent.

7. The pharmaceutical composition according to claim 1, which contains about 0.1 mg/ml to about 5 mg/ml.

8. The pharmaceutical composition according to claim 1, which contains about 0.4 mg/ml to 2 mg/ml.

9. A method of inhibiting angiogenesis comprising administering a pharmaceutically effective amount of the pharmaceutical composition according to claim 1 to a mammal.

10. A method for treating ophthalmic diseases in a subject in need thereof, comprising administering a pharmaceutically effective amount of the pharmaceutical composition according to claim 1 to said subject.

11. A method according to claim 10 for restoring visual acuity and/or corneal sensitivity.

12. The method according to claim 10, comprising administering one to two drops per day and per affected eye of the pharmaceutical composition according to claim 1 to said subject.

13. The method according to claim 10, wherein said pharmaceutical composition comprises about 0.1 mg/ml to about 5 mg/ml of the active agent.

14. A method for treating corneal graft rejection in a subject in need thereof, comprising administering a pharmaceutically effective amount of the pharmaceutical composition according to claim 1 to said subject.

15. The method according to claim 14, comprising administering one to two drops per day and per affected eye of a pharmaceutical composition according to claim 1, wherein said composition comprises about 0.4 mg/ml to about 2 mg/ml of the active agent.

16. A method according to claim 14 for treating corneal graft rejection in a subject having experienced corneal lesions leading to neovascularization.

17. A method according to claim 14 for treating corneal graft rejection in a subject suffering from keratitis or keratouveitis, wherein said keratitis or keratouveitis is due to contact lens, bacteria, microorganisms, viruses, protozoa, immunologic diseases, or due to trauma and prior surgery, alkali burns, graft rejection and degenerative disorders.

18. A method for treating neovascular glaucoma or retinopathy of prematurity in a subject in need thereof, comprising administering a pharmaceutically effective amount of the pharmaceutical composition according to claim 1 to said subject.

19. A method for treating age related macular degeneration in a subject in need thereof, comprising administering a pharmaceutically effective amount of the pharmaceutical composition according to claim 1 to said subject.

20. A method for treating diabetic retinopathy in a subject in need thereof, comprising administering a pharmaceutically effective amount of the pharmaceutical composition according to claim 1 to said subject.

21. A method for treating dermatological diseases in a subject in need thereof, comprising administering a pharmaceutically effective amount of the pharmaceutical composition according to claim 1 to said subject.

22. A method for treating psoriasis or rosacea in a subject in need thereof, comprising administering a pharmaceutically effective amount of the pharmaceutical composition according to claim 1 to said subject.

23. A pharmaceutical composition comprising as an active agent at least one nucleotide sequence selected from the group consisting of a nucleic acid sequence consisting of at least twelve contiguous nucleotides of the nucleic acid molecule SEQ ID NO 30 and a derivative of said nucleic acid sequence capable of hybridizing with IRS-1 sequence at a temperature from 42° C. to 65° C., 2×SSC and 0.1% SDS.

24. The pharmaceutical composition according to claim 23, wherein said nucleic acid sequence consisting of at least twelve contiguous nucleotides of the nucleic acid molecule SEQ ID NO 30 is selected from the group consisting of SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44 and fragments thereof comprising at least twelve contiguous nucleotides.

* * * * *

SEQUENCE LISTING

```
<160> NUMBER OF SEQ ID NOS: 45

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgatgtgac gctactgatg agtccgtgag gacgaaactc tggcctag                    48

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tatccggagg gctcgccatg ctgctgcgga gcaga                                  35

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tatccggagg gctcgccatg ctgct                                             25

<210> SEQ ID NO 4
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 4
tcgccatgct gctgcggagc aga                                          23

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tatccggagg gcctgccatg ctgct                                        25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tatccggagg gcctgccatg ctgc                                         24

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tatccggagg gcctgccatg ctg                                          23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tatccggagg gcctgccatg ct                                           22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tatccggagg gcctgccatg c                                            21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
tatccggagg gcctgccatg                                                      20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tatccggagg gcctgccat                                                       19

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tatccggagg gcctgcca                                                        18

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tatccggagg gcctgcc                                                         17

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tatccggagg gcctgc                                                          16

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tatccggagg gcctg                                                           15

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tatccggagg gcct                                                        14

<210> SEQ ID NO 17
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tatccggagg gcc                                                         13

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tatccggagg gc                                                          12

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccggagggcc tgccatgctg ct                                               22

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gagggcctgc catgctgct                                                   19

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggcctgccat gctgct                                                      16

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 22
ctgccatgct gct                                                              13

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgccatgctg ct                                                               12

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tttttttttt ttgg                                                             14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tttttttttt ttag                                                             14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tttttttttt ttcg                                                             14

<210> SEQ ID NO 27
<211> LENGTH: 326
<212> TYPE: DNA
<213> ORGANISM: Homo sapiens

<400> SEQUENCE: 27
gtgccgagct gagttcctta taagaattaa tcttaatttt gtattttttc ctgtaagaca           60
ataggccatg ttaattaaac tgaagaagga tatatttggc tgggtgtttt caaatgtcag          120
cttaaaattg gtaattgaat ggaagcaaaa ttataagaag aggaaattaa agtcttccat          180
tgcatgtatt gtaaacagaa ggagatgggt gattccttca attcaaaagc tctctttgga          240
atgaacaatg tgggcgtttg taaattctgg aaatgtcttt ctattcataa taaactagat          300
actgttgatc ttttaaaaaa aaaaaa                                               326

<210> SEQ ID NO 28
<211> LENGTH: 5800
```

```
<212> TYPE: DNA
<213> ORGANISM: Homo sapiens
<220> FEATURE:
<221> NAME/KEY: CDS
<222> LOCATION: (1022)..(4750)

<400> SEQUENCE: 28
cggcggcgcg gtcggagggg gccggcgcgc agagccagac gccgccgctt gttttggttg      60
gggctctcgg caactctccg aggaggagga ggaggaggga ggaggggaga agtaactgca     120
gcggcagcgc ctcccgagga acaggcgtct tccccgaacc cttcccaaac ctcccccatc     180
ccctctcgcc cttgtcccct cccctcctcc ccagccgcct ggagcgaggg gcagggatga     240
gtctgtccct ccggccggtc cccagctgca gtggctgccc ggtatcgttt cgcatggaaa     300
agccactttc tccacccgcc gagatgggcc cggatggggg ctgcagagga cgcgcccgcg     360
ggcggcggca gcagcagcag cagcagcagc agcaacagca acagccgcag cgccgcggtc     420
tctgcgactg agctggtatt tgggcggctg gtggcggctg ggacggttgg ggggtgggag     480
gaggcgaagg aggagggaga accccgtgca acgttgggac ttggcaaccc gcctcccccct     540 gcccaaggat atttaatttg cctcgggaat cgctgcttcc agaggggaac tcaggaggga     600
aggcgcgcgc gcgcgcgcgc tcctggaggg gcaccgcagg gacccccgac tgtcgcctcc     660
ctgtgccgga ctccagccgg ggcgacgaga gatgcatctt cgctccttcc tggtggcggc     720
ggcggctgag aggagacttg gctctcggag gatcggggct gccctcaccc cggacgcact     780
gcctccccgc cgggcgtgaa cgcccgaaa actccggtcg gctctctcc tgggctcagc      840 agctgcgtcc tccttcagct gcccctcccc ggcgcggggg gcggcgtgga tttcagagtc     900
ggggtttctg ctgcctccag ccctgtttgc atgtgccggg ccgcggcgag gagcctccgc     960
cccccacccg gttgtttttc ggagcctccc tctgctcagc gttggtggtg gcggtggcag    1020 c atg gcg agc cct ccg gag agc gat ggc ttc tcg gac gtg cgc aag gtg     1069
  Met Ala Ser Pro Pro Glu Ser Asp Gly Phe Ser Asp Val Arg Lys Val
   1               5                  10                  15 ggc tac ctg cgc aaa ccc aag agc atg cac aaa cgc ttc ttc gta ctg       1117
Gly Tyr Leu Arg Lys Pro Lys Ser Met His Lys Arg Phe Phe Val Leu
             20                  25                  30 cgc gcg gcc agc gag gct ggg ggc ccg gcg cgc ctc gag tac tac gag       1165
Arg Ala Ala Ser Glu Ala Gly Gly Pro Ala Arg Leu Glu Tyr Tyr Glu
         35                  40                  45 aac gag aag aag tgg cgg cac aag tcg agc gcc ccc aaa cgc tcg atc       1213
Asn Glu Lys Lys Trp Arg His Lys Ser Ser Ala Pro Lys Arg Ser Ile
     50                  55                  60 ccc ctt gag agc tgc ttc aac atc aac aag cgg gct gac tcc aag aac       1261
Pro Leu Glu Ser Cys Phe Asn Ile Asn Lys Arg Ala Asp Ser Lys Asn
65                  70                  75                  80 aag cac ctg gtg gct ctc tac acc cgg gac gag cac ttt gcc atc gcg       1309
Lys His Leu Val Ala Leu Tyr Thr Arg Asp Glu His Phe Ala Ile Ala
                 85                  90                  95 gcg gac agc gag gcc gag caa gac agc tgg tac cag gct ctc cta cag       1357
Ala Asp Ser Glu Ala Glu Gln Asp Ser Trp Tyr Gln Ala Leu Leu Gln
            100                 105                 110 ctg cac aac cgt gct aag ggc cac cac gac gga gct gcg gcc ctc ggg       1405
Leu His Asn Arg Ala Lys Gly His His Asp Gly Ala Ala Ala Leu Gly
        115                 120                 125 gcg gga ggt ggt ggg ggc agc tgc agc ggc agc tcc ggc ctt ggt gag       1453
Ala Gly Gly Gly Gly Gly Ser Cys Ser Gly Ser Ser Gly Leu Gly Glu
    130                 135                 140 gct ggg gag gac ttg agc tac ggt gac gtg ccc cca gga ccc gca ttc       1501
```

```
Ala Gly Glu Asp Leu Ser Tyr Gly Asp Val Pro Pro Gly Pro Ala Phe
145                 150                 155                 160 aaa gag gtc tgg caa gtg atc ctg aag ccc aag ggc ctg ggt cag aca        1549
Lys Glu Val Trp Gln Val Ile Leu Lys Pro Lys Gly Leu Gly Gln Thr
                165                 170                 175 aag aac ctg att ggt atc tac cgc ctt tgc ctg acc agc aag acc atc        1597
Lys Asn Leu Ile Gly Ile Tyr Arg Leu Cys Leu Thr Ser Lys Thr Ile
            180                 185                 190 agc ttc gtg aag ctg aac tcg gag gca gcg gcc gtg gtg ctg cag ctg        1645
Ser Phe Val Lys Leu Asn Ser Glu Ala Ala Ala Val Val Leu Gln Leu
        195                 200                 205 atg aac atc agg cgc tgt ggc cac tcg gaa aac ttc ttc ttc atc gag        1693
Met Asn Ile Arg Arg Cys Gly His Ser Glu Asn Phe Phe Phe Ile Glu
    210                 215                 220 gtg ggc cgt tct gcc gtg acg ggg ccc ggg gag ttc tgg atg cag gtg        1741
Val Gly Arg Ser Ala Val Thr Gly Pro Gly Glu Phe Trp Met Gln Val
225                 230                 235                 240 gat gac tct gtg gtg gcc cag aac atg cac gag acc atc ctg gag gcc        1789
Asp Asp Ser Val Val Ala Gln Asn Met His Glu Thr Ile Leu Glu Ala
                245                 250                 255 atg cgg gcc atg agt gat gag ttc cgc cct cgc agc aag agc cag tcc        1837
Met Arg Ala Met Ser Asp Glu Phe Arg Pro Arg Ser Lys Ser Gln Ser
                260                 265                 270 tcg tcc aac tgc tct aac ccc atc agc gtc ccc ctg cgc cgg cac cat        1885
Ser Ser Asn Cys Ser Asn Pro Ile Ser Val Pro Leu Arg Arg His His
            275                 280                 285 ctc aac aat ccc ccg ccc agc cag gtg ggg ctg acc cgc cga tca cgc        1933
Leu Asn Asn Pro Pro Pro Ser Gln Val Gly Leu Thr Arg Arg Ser Arg
        290                 295                 300 act gag agc atc acc gcc acc tcc ccg gcc agc atg gtg ggc ggg aag        1981
Thr Glu Ser Ile Thr Ala Thr Ser Pro Ala Ser Met Val Gly Gly Lys
305                 310                 315                 320 cca ggc tcc ttc cgt gtc cgc gcc tcc agt gac ggc gaa ggc acc atg        2029
Pro Gly Ser Phe Arg Val Arg Ala Ser Ser Asp Gly Glu Gly Thr Met
                325                 330                 335 tcc cgc cca gcc tcg gtg gac ggc agc cct gtg agt ccc agc acc aac        2077
Ser Arg Pro Ala Ser Val Asp Gly Ser Pro Val Ser Pro Ser Thr Asn
                340                 345                 350 aga acc cac gcc cac cgg cat cgg ggc agc gcc cgg ctg cac ccc ccg        2125
Arg Thr His Ala His Arg His Arg Gly Ser Ala Arg Leu His Pro Pro
            355                 360                 365 ctc aac cac agc cgc tcc atc ccc atg ccg gct tcc cgc tgc tcg cct        2173
Leu Asn His Ser Arg Ser Ile Pro Met Pro Ala Ser Arg Cys Ser Pro
        370                 375                 380 tcg gcc acc agc ccg gtc agt ctg tcg tcc agt agc acc agt ggc cat        2221
Ser Ala Thr Ser Pro Val Ser Leu Ser Ser Ser Thr Ser Gly His
385                 390                 395                 400 ggc tcc acc tcg gat tgt ctc ttc cca cgg cga tct agt gct tcg gtg        2269
Gly Ser Thr Ser Asp Cys Leu Phe Pro Arg Arg Ser Ser Ala Ser Val
                405                 410                 415 tct ggt tcc ccc agc gat ggc ggt ttc atc tcc tcg gat gag tat ggc        2317
Ser Gly Ser Pro Ser Asp Gly Gly Phe Ile Ser Ser Asp Glu Tyr Gly
                420                 425                 430 tcc agt ccc tgc gat ttc cgg agt tcc ttc cgc agt gtc act ccg gat        2365
Ser Ser Pro Cys Asp Phe Arg Ser Ser Phe Arg Ser Val Thr Pro Asp
            435                 440                 445 tcc ctg ggc cac acc cca cca gcc cgc ggt gag gag gag cta agc aac        2413
Ser Leu Gly His Thr Pro Pro Ala Arg Gly Glu Glu Glu Leu Ser Asn
        450                 455                 460
```

-continued

| | | |
|---|---|---|
| tat atc tgc atg ggt ggc aag ggg ccc tcc acc ctg acc gcc ccc aac<br>Tyr Ile Cys Met Gly Gly Lys Gly Pro Ser Thr Leu Thr Ala Pro Asn<br>465                      470                      475                      480 | 2461 |
| ggt cac tac att ttg tct cgg ggt ggc aat ggc cac cgc tgc acc cca<br>Gly His Tyr Ile Leu Ser Arg Gly Gly Asn Gly His Arg Cys Thr Pro<br>                      485                      490                      495 | 2509 |
| gga aca ggc ttg ggc acg agt cca gcc ttg gct ggg gat gaa gca gcc<br>Gly Thr Gly Leu Gly Thr Ser Pro Ala Leu Ala Gly Asp Glu Ala Ala<br>            500                      505                      510 | 2557 |
| agt gct gca gat ctg gat aat cgg ttc cga aag aga act cac tcg gca<br>Ser Ala Ala Asp Leu Asp Asn Arg Phe Arg Lys Arg Thr His Ser Ala<br>515                      520                      525 | 2605 |
| ggc aca tcc cct acc att acc cac cag aag acc ccg tcc cag tcc tca<br>Gly Thr Ser Pro Thr Ile Thr His Gln Lys Thr Pro Ser Gln Ser Ser<br>        530                      535                      540 | 2653 |
| gtg gct tcc att gag gag tac aca gag atg atg cct gcc tac cca cca<br>Val Ala Ser Ile Glu Glu Tyr Thr Glu Met Met Pro Ala Tyr Pro Pro<br>545                      550                      555                      560 | 2701 |
| gga ggt ggc agt gga ggc cga ctg ccg gga cac agg cac tcc gcc ttc<br>Gly Gly Gly Ser Gly Gly Arg Leu Pro Gly His Arg His Ser Ala Phe<br>                      565                      570                      575 | 2749 |
| gtg ccc acc cgc tcc tac cca gag gag ggt ctg gaa atg cac ccc ttg<br>Val Pro Thr Arg Ser Tyr Pro Glu Glu Gly Leu Glu Met His Pro Leu<br>        580                      585                      590 | 2797 |
| gag cgt cgg ggg ggg cac cac cgc cca gac agc tcc acc ctc cac acg<br>Glu Arg Arg Gly Gly His His Arg Pro Asp Ser Ser Thr Leu His Thr<br>              595                      600                      605 | 2845 |
| gat gat ggc tac atg ccc atg tcc cca ggg gtg gcc cca gtg ccc agt<br>Asp Asp Gly Tyr Met Pro Met Ser Pro Gly Val Ala Pro Val Pro Ser<br>610                      615                      620 | 2893 |
| ggc cga aag ggc agt gga gac tat atg ccc atg agc ccc aag agc gta<br>Gly Arg Lys Gly Ser Gly Asp Tyr Met Pro Met Ser Pro Lys Ser Val<br>625                      630                      635                      640 | 2941 |
| tct gcc cca cag cag atc atc aat ccc atc aga cgc cat ccc cag aga<br>Ser Ala Pro Gln Gln Ile Ile Asn Pro Ile Arg Arg His Pro Gln Arg<br>                      645                      650                      655 | 2989 |
| gtg gac ccc aat ggc tac atg atg atg tcc ccc agc ggt ggc tgc tct<br>Val Asp Pro Asn Gly Tyr Met Met Met Ser Pro Ser Gly Gly Cys Ser<br>            660                      665                      670 | 3037 |
| cct gac att gga ggt ggc ccc agc agc agc agc agc agc aac gcc<br>Pro Asp Ile Gly Gly Gly Pro Ser Ser Ser Ser Ser Ser Asn Ala<br>        675                      680                      685 | 3085 |
| gtc cct tcc ggg acc agc tat gga aag ctg tgg aca aac ggg gta ggg<br>Val Pro Ser Gly Thr Ser Tyr Gly Lys Leu Trp Thr Asn Gly Val Gly<br>690                      695                      700 | 3133 |
| ggc cac cac tct cat gtc ttg cct cac ccc aaa ccc cca gtg gag agc<br>Gly His His Ser His Val Leu Pro His Pro Lys Pro Pro Val Glu Ser<br>705                      710                      715                      720 | 3181 |
| agc ggt ggt aag ctc tta cct tgc aca ggt gac tac atg aac atg tca<br>Ser Gly Gly Lys Leu Leu Pro Cys Thr Gly Asp Tyr Met Asn Met Ser<br>                      725                      730                      735 | 3229 |
| cca gtg ggg gac tcc aac acc agc agc ccc tcc gac tgc tac tac ggc<br>Pro Val Gly Asp Ser Asn Thr Ser Ser Pro Ser Asp Cys Tyr Tyr Gly<br>        740                      745                      750 | 3277 |
| cct gag gac ccc cag cac aag cca gtc ctc tcc tac tac tca ttg cca<br>Pro Glu Asp Pro Gln His Lys Pro Val Leu Ser Tyr Tyr Ser Leu Pro<br>755                      760                      765 | 3325 |
| aga tcc ttt aag cac acc cag cgc ccc ggg gag ccg gag gag ggt gcc<br>Arg Ser Phe Lys His Thr Gln Arg Pro Gly Glu Pro Glu Glu Gly Ala<br>770                      775                      780 | 3373 |

-continued

```
cgg cat cag cac ctc cgc ctt tcc act agc tct ggt cgc ctt ctc tat    3421
Arg His Gln His Leu Arg Leu Ser Thr Ser Ser Gly Arg Leu Leu Tyr
785                 790                 795                 800 gct gca aca gca gat gat tct tcc tct tcc acc agc agc gac agc ctg    3469
Ala Ala Thr Ala Asp Asp Ser Ser Ser Ser Thr Ser Ser Asp Ser Leu
                805                 810                 815 ggt ggg gga tac tgc ggg gct agg ctg gag ccc agc ctt cca cat ccc    3517
Gly Gly Gly Tyr Cys Gly Ala Arg Leu Glu Pro Ser Leu Pro His Pro
            820                 825                 830 cac cat cag gtt ctg cag ccc cat ctg cct cga aag gtg gac aca gct    3565
His His Gln Val Leu Gln Pro His Leu Pro Arg Lys Val Asp Thr Ala
        835                 840                 845 gct cag acc aat agc cgc ctg gcc cgg ccc acg agg ctg tcc ctg ggg    3613
Ala Gln Thr Asn Ser Arg Leu Ala Arg Pro Thr Arg Leu Ser Leu Gly
    850                 855                 860 gat ccc aag gcc agc acc tta cct cgg gcc cga gag cag cag cag cag    3661
Asp Pro Lys Ala Ser Thr Leu Pro Arg Ala Arg Glu Gln Gln Gln Gln
865                 870                 875                 880 cag cag ccc ttg ctg cac cct cca gag ccc aag agc ccg ggg gaa tat    3709
Gln Gln Pro Leu Leu His Pro Pro Glu Pro Lys Ser Pro Gly Glu Tyr
                885                 890                 895 gtc aat att gaa ttt ggg agt gat cag tct ggc tac ttg tct ggc ccg    3757
Val Asn Ile Glu Phe Gly Ser Asp Gln Ser Gly Tyr Leu Ser Gly Pro
            900                 905                 910 gtg gct ttc cac agc tca cct tct gtc agg tgt cca tcc cag ctc cag    3805
Val Ala Phe His Ser Ser Pro Ser Val Arg Cys Pro Ser Gln Leu Gln
        915                 920                 925 cca gct ccc aga gag gaa gag act ggc act gag gag tac atg aag atg    3853
Pro Ala Pro Arg Glu Glu Glu Thr Gly Thr Glu Glu Tyr Met Lys Met
    930                 935                 940 gac ctg ggg ccg ggc cgg agg gca gcc tgg cag gag agc act ggg gtc    3901
Asp Leu Gly Pro Gly Arg Arg Ala Ala Trp Gln Glu Ser Thr Gly Val
945                 950                 955                 960 gag atg ggc aga ctg ggc cct gca cct ccc ggg gct gct agc att tgc    3949
Glu Met Gly Arg Leu Gly Pro Ala Pro Pro Gly Ala Ala Ser Ile Cys
                965                 970                 975 agg cct acc cgg gca gtg ccc agc agc cgg ggt gac tac atg acc atg    3997
Arg Pro Thr Arg Ala Val Pro Ser Ser Arg Gly Asp Tyr Met Thr Met
            980                 985                 990 cag atg agt tgt ccc cgt cag agc tac gtg gac acc tcg cca gct gcc    4045
Gln Met Ser Cys Pro Arg Gln Ser Tyr Val Asp Thr Ser Pro Ala Ala
        995                 1000                1005 cct gta agc tat gct gac atg cga aca ggc att gct gca gag gag        4090
Pro Val Ser Tyr Ala Asp Met Arg Thr Gly Ile Ala Ala Glu Glu
    1010                1015                1020 gtg agc ctg ccc agg gcc acc atg gct gct gcc tcc tca tcc tca        4135
Val Ser Leu Pro Arg Ala Thr Met Ala Ala Ala Ser Ser Ser Ser
1025                1030                1035 gca gcc tct gct tcc ccg act ggg cct caa ggg gca gca gag ctg        4180
Ala Ala Ser Ala Ser Pro Thr Gly Pro Gln Gly Ala Ala Glu Leu
    1040                1045                1050 gct gcc cac tcg tcc ctg ctg ggg ggc cca caa gga cct ggg ggc        4225
Ala Ala His Ser Ser Leu Leu Gly Gly Pro Gln Gly Pro Gly Gly
    1055                1060                1065 atg agc gcc ttc acc cgg gtg aac ctc agt cct aac cgc aac cag        4270
Met Ser Ala Phe Thr Arg Val Asn Leu Ser Pro Asn Arg Asn Gln
1070                1075                1080 agt gcc aaa gtg atc cgt gca gac cca caa ggg tgc cgg cgg agg        4315
Ser Ala Lys Val Ile Arg Ala Asp Pro Gln Gly Cys Arg Arg Arg
```

```
                     1085                     1090                     1095
cat agc tcc gag act ttc tcc tca aca ccc agt gcc acc cgg gtg         4360
His Ser Ser Glu Thr Phe Ser Ser Thr Pro Ser Ala Thr Arg Val
    1100                 1105                     1110 ggc aac aca gtg ccc ttt gga gcg ggg gca gca gta ggg ggc ggt         4405
Gly Asn Thr Val Pro Phe Gly Ala Gly Ala Ala Val Gly Gly Gly
    1115                 1120                     1125 ggc ggt agc agc agc agc agc gag gat gtg aaa cgc cac agc tct         4450
Gly Gly Ser Ser Ser Ser Ser Glu Asp Val Lys Arg His Ser Ser
    1130                 1135                     1140 gct tcc ttt gag aat gtg tgg ctg agg cct ggg gag ctt ggg gga         4495
Ala Ser Phe Glu Asn Val Trp Leu Arg Pro Gly Glu Leu Gly Gly
    1145                 1150                     1155 gcc ccc aag gag cca gcc aaa ctg tgt ggg gct gct ggg ggt ttg         4540
Ala Pro Lys Glu Pro Ala Lys Leu Cys Gly Ala Ala Gly Gly Leu
    1160                 1165                     1170 gag aat ggt ctt aac tac ata gac ctg gat ttg gtc aag gac ttc         4585
Glu Asn Gly Leu Asn Tyr Ile Asp Leu Asp Leu Val Lys Asp Phe
    1175                 1180                     1185 aaa cag tgc cct cag gag tgc acc cct gaa ccg cag cct ccc cca         4630
Lys Gln Cys Pro Gln Glu Cys Thr Pro Glu Pro Gln Pro Pro Pro
    1190                 1195                     1200 ccc cca ccc cct cat caa ccc ctg ggc agc ggt gag agc agc tcc         4675
Pro Pro Pro Pro His Gln Pro Leu Gly Ser Gly Glu Ser Ser Ser
    1205                 1210                     1215 acc cgc cgc tca agt gag gat tta agc gcc tat gcc agc atc agt         4720
Thr Arg Arg Ser Ser Glu Asp Leu Ser Ala Tyr Ala Ser Ile Ser
    1220                 1225                     1230 ttc cag aag cag cca gag gac cgt cag tag ctcaactgga catcacagca       4770
Phe Gln Lys Gln Pro Glu Asp Arg Gln
    1235                 1240 gaatgaagac ctaaatgacc tcagcaaatc tccttctaac tcatgggtac ccagactcta    4830
aatatttcat gattcacaac taggacctca tatcttcctc atcagtagat ggtacgatgc    4890
atccatttca gtttgtttac tttatccaat cctcaggatt tcattgactg aactgcacgt    4950
tctatattgt gccaagcgaa aaaaaaaaat gcactgtgac accagaataa tgagtctgca    5010
taaacttcat cttcaacctt aaggacttag ctggccacag tgagctgatg tgccaccac     5070 cgtgtcatga gagaatgggt ttactctcaa tgcattttca agatacattt catctgctgc    5130
tgaaactgtg tacgacaaag catcattgta aattatttca tacaaaactg ttcacgttgg    5190
gtggagagag tattaaatat ttaacatagg ttttgattta tatgtgtaat tttttaaatg    5250
aaaatgtaac ttttcttaca gcacatcttt tttttggatg tgggatggag gtatacaatg    5310
ttctgttgta aagagtggag caaatgctta aaacaaggct taaagagta gaataggta     5370 tgatccttgt tttaagattg taattcagaa aacataatat aagaatcata gtgccataga    5430
tggttctcaa ttgtatagtt atatttgctg atactatctc ttgtcatata aacctgatgt    5490
tgagctgagt tccttataag aattaatctt aattttgtat ttttttcctgt aagacaatag   5550 gccatgttaa ttaaactgaa gaaggatata tttggctggg tgttttcaaa tgtcagctta    5610
aaattggtaa ttgaatggaa gcaaaattat aagaagagga aattaaagtc ttccattgca    5670
tgtattgtaa acagaaggag atgggtgatt ccttcaattc aaaagctctc tttggaatga    5730
acaatgtggg cgtttgtaaa ttctggaaat gtctttctat tcataataaa ctagatactg    5790
ttgatctttt                                                           5800
```

<210> SEQ ID NO 29
<211> LENGTH: 1242
<212> TYPE: PRT
<213> ORGANISM: Homo sapiens

<400> SEQUENCE: 29

```
Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
    130                 135                 140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Ala Val Val Leu Gln Leu
        195                 200                 205

Met Asn Ile Arg Arg Cys Gly His Ser Glu Asn Phe Phe Phe Ile Glu
    210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
            260                 265                 270

Ser Ser Asn Cys Ser Asn Pro Ile Ser Val Pro Leu Arg Arg His His
        275                 280                 285

Leu Asn Asn Pro Pro Ser Gln Val Gly Leu Thr Arg Arg Ser Arg
    290                 295                 300

Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
                325                 330                 335

Ser Arg Pro Ala Ser Val Asp Gly Ser Pro Val Ser Pro Ser Thr Asn
            340                 345                 350

Arg Thr His Ala His Arg His Arg Gly Ser Ala Arg Leu His Pro Pro
        355                 360                 365

Leu Asn His Ser Arg Ser Ile Pro Met Pro Ala Ser Arg Cys Ser Pro
    370                 375                 380
```

-continued

```
Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ser Ala Ser Val
                405                 410                 415

Ser Gly Ser Pro Ser Asp Gly Gly Phe Ile Ser Ser Asp Glu Tyr Gly
                420                 425                 430

Ser Ser Pro Cys Asp Phe Arg Ser Ser Phe Arg Ser Val Thr Pro Asp
                435                 440                 445

Ser Leu Gly His Thr Pro Pro Ala Arg Gly Glu Glu Glu Leu Ser Asn
            450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Gly Asn Gly His Arg Cys Thr Pro
                485                 490                 495

Gly Thr Gly Leu Gly Thr Ser Pro Ala Leu Ala Gly Asp Glu Ala Ala
                500                 505                 510

Ser Ala Ala Asp Leu Asp Asn Arg Phe Arg Lys Arg Thr His Ser Ala
            515                 520                 525

Gly Thr Ser Pro Thr Ile Thr His Gln Lys Thr Pro Ser Gln Ser Ser
            530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
                565                 570                 575

Val Pro Thr Arg Ser Tyr Pro Glu Glu Gly Leu Glu Met His Pro Leu
                580                 585                 590

Glu Arg Arg Gly Gly His His Arg Pro Asp Ser Ser Thr Leu His Thr
            595                 600                 605

Asp Asp Gly Tyr Met Pro Met Ser Pro Gly Val Ala Pro Val Pro Ser
            610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
                645                 650                 655

Val Asp Pro Asn Gly Tyr Met Met Met Ser Pro Ser Gly Gly Cys Ser
                660                 665                 670

Pro Asp Ile Gly Gly Gly Pro Ser Ser Ser Ser Ser Ser Asn Ala
            675                 680                 685

Val Pro Ser Gly Thr Ser Tyr Gly Lys Leu Trp Thr Asn Gly Val Gly
            690                 695                 700

Gly His His Ser His Val Leu Pro His Pro Lys Pro Pro Val Glu Ser
705                 710                 715                 720

Ser Gly Gly Lys Leu Leu Pro Cys Thr Gly Asp Tyr Met Asn Met Ser
                725                 730                 735

Pro Val Gly Asp Ser Asn Thr Ser Ser Pro Ser Asp Cys Tyr Tyr Gly
                740                 745                 750

Pro Glu Asp Pro Gln His Lys Pro Val Leu Ser Tyr Tyr Ser Leu Pro
                755                 760                 765

Arg Ser Phe Lys His Thr Gln Arg Pro Gly Glu Pro Glu Glu Gly Ala
            770                 775                 780

Arg His Gln His Leu Arg Leu Ser Thr Ser Ser Gly Arg Leu Leu Tyr
785                 790                 795                 800

Ala Ala Thr Ala Asp Asp Ser Ser Ser Ser Thr Ser Ser Asp Ser Leu
```

-continued

```
               805                 810                 815
Gly Gly Gly Tyr Cys Gly Ala Arg Leu Glu Pro Ser Leu Pro His Pro
            820                 825                 830

His His Gln Val Leu Gln Pro His Leu Pro Arg Lys Val Asp Thr Ala
            835                 840                 845

Ala Gln Thr Asn Ser Arg Leu Ala Arg Pro Thr Arg Leu Ser Leu Gly
        850                 855                 860

Asp Pro Lys Ala Ser Thr Leu Pro Arg Ala Arg Glu Gln Gln Gln Gln
865                 870                 875                 880

Gln Gln Pro Leu Leu His Pro Pro Glu Pro Lys Ser Pro Gly Glu Tyr
            885                 890                 895

Val Asn Ile Glu Phe Gly Ser Asp Gln Ser Gly Tyr Leu Ser Gly Pro
            900                 905                 910

Val Ala Phe His Ser Ser Pro Ser Val Arg Cys Pro Ser Gln Leu Gln
            915                 920                 925

Pro Ala Pro Arg Glu Glu Thr Gly Thr Glu Tyr Met Lys Met
            930                 935                 940

Asp Leu Gly Pro Gly Arg Arg Ala Ala Trp Gln Glu Ser Thr Gly Val
945                 950                 955                 960

Glu Met Gly Arg Leu Gly Pro Ala Pro Pro Gly Ala Ala Ser Ile Cys
                965                 970                 975

Arg Pro Thr Arg Ala Val Pro Ser Ser Arg Gly Asp Tyr Met Thr Met
                980                 985                 990

Gln Met Ser Cys Pro Arg Gln Ser  Tyr Val Asp Thr Ser  Pro Ala Ala
                995                 1000                1005

Pro Val  Ser Tyr Ala Asp Met  Arg Thr Gly Ile Ala  Ala Glu Glu
        1010                1015                1020

Val Ser  Leu Pro Arg Ala Thr  Met Ala Ala Ala Ser  Ser Ser Ser
        1025                1030                1035

Ala Ala  Ser Ala Ser Pro Thr  Gly Pro Gln Gly Ala  Ala Glu Leu
        1040                1045                1050

Ala Ala  His Ser Ser Leu Leu  Gly Gly Pro Gln Gly  Pro Gly Gly
        1055                1060                1065

Met Ser  Ala Phe Thr Arg Val  Asn Leu Ser Pro Asn  Arg Asn Gln
        1070                1075                1080

Ser Ala  Lys Val Ile Arg Ala  Asp Pro Gln Gly Cys  Arg Arg Arg
        1085                1090                1095

His Ser  Ser Glu Thr Phe Ser  Ser Thr Pro Ser Ala  Thr Arg Val
        1100                1105                1110

Gly Asn  Thr Val Pro Phe Gly  Ala Gly Ala Ala Val  Gly Gly Gly
        1115                1120                1125

Gly Gly  Ser Ser Ser Ser Ser  Glu Asp Val Lys Arg  His Ser Ser
        1130                1135                1140

Ala Ser  Phe Glu Asn Val Trp  Leu Arg Pro Gly Glu  Leu Gly Gly
        1145                1150                1155

Ala Pro  Lys Glu Pro Ala Lys  Leu Cys Gly Ala Ala  Gly Gly Leu
        1160                1165                1170

Glu Asn  Gly Leu Asn Tyr Ile  Asp Leu Asp Leu Val  Lys Asp Phe
        1175                1180                1185

Lys Gln  Cys Pro Gln Glu Cys  Thr Pro Glu Pro Gln  Pro Pro Pro
        1190                1195                1200

Pro Pro  Pro Pro His Gln Pro  Leu Gly Ser Gly Glu  Ser Ser Ser
        1205                1210                1215
```

```
Thr Arg Arg Ser Ser Glu Asp Leu Ser Ala Tyr Ala Ser Ile Ser
    1220                1225                1230

Phe Gln Lys Gln Pro Glu Asp Arg Gln
    1235                1240
```

<210> SEQ ID NO 30
<211> LENGTH: 150
<212> TYPE: DNA
<213> ORGANISM: Homo sapiens

<400> SEQUENCE: 30

```
tagtactcga ggcgcgccgg gcccccagcc tcgctggccg cgcgcagtac gaagaagcgt    60
ttgtgcatgc tcttgggttt gcgcaggtag cccaccttgc gcacgtccga gaagccatcg   120
ctctccggag ggctcgccat gctgccaccg                                    150
```

<210> SEQ ID NO 31
<211> LENGTH: 24
<212> TYPE: DNA
<213> ORGANISM: Homo sapiens

<400> SEQUENCE: 31

```
tctccggagg gctcgccatg ctgc                                           24
```

<210> SEQ ID NO 32
<211> LENGTH: 25
<212> TYPE: DNA
<213> ORGANISM: Homo sapiens

<400> SEQUENCE: 32

```
cggagggctc gccatgctgc caccg                                          25
```

<210> SEQ ID NO 33
<211> LENGTH: 24
<212> TYPE: DNA
<213> ORGANISM: Homo sapiens

<400> SEQUENCE: 33

```
cggagggctc gccatgctgc cacc                                           24
```

<210> SEQ ID NO 34
<211> LENGTH: 23
<212> TYPE: DNA
<213> ORGANISM: Homo sapiens

<400> SEQUENCE: 34

```
cggagggctc gccatgctgc cac                                            23
```

<210> SEQ ID NO 35
<211> LENGTH: 22
<212> TYPE: DNA
<213> ORGANISM: Homo sapiens

<400> SEQUENCE: 35

```
cggagggctc gccatgctgc ca                                             22
```

<210> SEQ ID NO 36
<211> LENGTH: 21
<212> TYPE: DNA
<213> ORGANISM: Homo sapiens

<400> SEQUENCE: 36

-continued

| | |
|---|---|
| cggagggctc gccatgctgc c | 21 |

<210> SEQ ID NO 37
<211> LENGTH: 20
<212> TYPE: DNA
<213> ORGANISM: Homo sapiens

<400> SEQUENCE: 37

| | |
|---|---|
| cggagggctc gccatgctgc | 20 |

<210> SEQ ID NO 38
<211> LENGTH: 27
<212> TYPE: DNA
<213> ORGANISM: Homo sapiens

<400> SEQUENCE: 38

| | |
|---|---|
| cgtccgagaa gccatcgctc tccggag | 27 |

<210> SEQ ID NO 39
<211> LENGTH: 27
<212> TYPE: DNA
<213> ORGANISM: Homo sapiens

<400> SEQUENCE: 39

| | |
|---|---|
| gcgcaggtag cccaccttgc gcacgtc | 27 |

<210> SEQ ID NO 40
<211> LENGTH: 16
<212> TYPE: DNA
<213> ORGANISM: Homo sapiens

<400> SEQUENCE: 40

| | |
|---|---|
| cccaccttgc gcacgt | 16 |

<210> SEQ ID NO 41
<211> LENGTH: 30
<212> TYPE: DNA
<213> ORGANISM: Homo sapiens

<400> SEQUENCE: 41

| | |
|---|---|
| gaagaagcgt tgtgcatgc tcttgggttt | 30 |

<210> SEQ ID NO 42
<211> LENGTH: 33
<212> TYPE: DNA
<213> ORGANISM: Homo sapiens

<400> SEQUENCE: 42

| | |
|---|---|
| gcccccagcc tcgctggccg cgcgcagtac gaa | 33 |

<210> SEQ ID NO 43
<211> LENGTH: 26
<212> TYPE: DNA
<213> ORGANISM: Homo sapiens

<400> SEQUENCE: 43

| | |
|---|---|
| tagtactcga ggcgcgccgg gccccc | 26 |

<210> SEQ ID NO 44
<211> LENGTH: 17
<212> TYPE: DNA
<213> ORGANISM: Homo sapiens

<400> SEQUENCE: 44

```
aggcgcgccg ggccccc                                                   17

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: a, c, g or t

<400> SEQUENCE: 45
tttttttttt ttmn                                                      14
```